(12) United States Patent
Farritor et al.

(10) Patent No.: US 7,755,774 B2
(45) Date of Patent: Jul. 13, 2010

(54) METHOD AND APPARATUS FOR NONCONTACT RELATIVE RAIL DISPLACEMENT, TRACK MODULUS AND STIFFNESS MEASUREMENT BY A MOVING RAIL VEHICLE

(75) Inventors: Shane Farritor, Lincoln, NE (US); Richard Arnold, Elkhorn, NE (US); Chris Norman, Littleton, CO (US)

(73) Assignee: Board of Regents of University of Nebraska, Lincoln, NE (US)

( * ) Notice: Subject to any disclaimer, the term of this patent is extended or adjusted under 35 U.S.C. 154(b) by 208 days.

(21) Appl. No.: 12/138,046

(22) Filed: Jun. 12, 2008

(65) Prior Publication Data

US 2008/0304083 A1 Dec. 11, 2008

Related U.S. Application Data

(63) Continuation of application No. 11/267,713, filed on Nov. 4, 2005, now Pat. No. 7,403,296.

(60) Provisional application No. 60/625,514, filed on Nov. 5, 2004.

(51) Int. Cl.
*G01B 11/14* (2006.01)

(52) U.S. Cl. .................................. 356/614; 356/622
(58) Field of Classification Search .......... 356/614–622
See application file for complete search history.

(56) References Cited

U.S. PATENT DOCUMENTS

| | | | | |
|---|---|---|---|---|
| 5,753,808 | A | * | 5/1998 | Johnson ........................ 73/146 |
| 6,119,353 | A | * | 9/2000 | Gr.o slashed.nskov ........ 33/1 Q |
| 6,647,891 | B2 | * | 11/2003 | Holmes et al. ................. 104/2 |

* cited by examiner

*Primary Examiner*—Michael P Stafira
(74) *Attorney, Agent, or Firm*—Shook Hardy & Bacon LLP

(57) ABSTRACT

An on-board, noncontact measurement system and method is disclosed for measuring track quality, vertical track stiffness and vertical track modulus for a portion of track underlying the rail vehicle. The system comprises first and second optical emitters mounted to the vehicle and configured to emit beams of light that are detectable on the underlying surface; a camera mounted to the vehicle for recording the distance between the beams of light as the vehicle travels along the surface, a mechanism for measuring the distance between the beams of light for a particular portion of the surface; and a mechanism for determining the vertical track stiffness or vertical track modulus for a particular portion of the track.

16 Claims, 7 Drawing Sheets

METHOD AND APPARATUS FOR NONCONTACT RELATIVE RAIL DISPLACEMENT, TRACK MODULUS AND STIFFNESS MEASUREMENT BY A MOVING RAIL VEHICLE

CROSS-REFERENCE TO RELATED APPLICATIONS

This application is a continuation of prior application Ser. No. 11/267,713, filed Nov. 4, 2005, which claims the benefit of U.S. Provisional Application No. 60/625,514, filed Nov. 5, 2004. Both of these applications are expressly incorporated by reference herein in their entirety.

TECHNICAL FIELD

The invention relates generally to methods and apparatus for surface modulus measurement and, more particularly, to methods and apparatus for noncontact, onboard, vertical track modulus measurement.

BACKGROUND OF THE INVENTION

Track quality is a major factor in railroad safety. One accepted indicator of track quality is the rail's vertical track modulus. Track modulus is defined as the coefficient of proportionality between the vertical rail deflection and the vertical contact pressure between the rail base and track foundation; it can be re-stated as the supporting force per unit length of rail, per unit rail deflection.

Railway track has several components that all contribute to track stiffness including the rail, subgrade, ballast, subballast, ties, and fasteners. The rail directly supports the train wheels and is supported on a rail pad and held in place with fasteners to crossties. The crossties rest on a layer of rock ballast and subballast used to provide drainage. The soil below the subballast is the subgrade.

The subgrade resilient modulus and subgrade thickness have the strongest influence on track modulus. These parameters depend upon the physical state of the soil, the stress state of the soil, and the soil type. Track modulus increases with increasing subgrade resilient modulus, and decreases with increasing subgrade layer thickness. Ballast layer thickness and fastener stiffness are the next most important factors. Increasing the thickness of the ballast layer and or increasing fastener stiffness will increase track modulus. This effect is caused by the load being spread over a larger area. It is desirable to measure the net effective track modulus, which includes all these factors.

Track modulus is important because it affects track performance and maintenance requirements. Both low track modulus and large variations in track modulus are undesirable. Low track modulus has been shown to cause differential settlement that then increases maintenance needs. Large variations in track modulus, such as those often found near bridges and crossings, have been shown to increase dynamic loading, which reduces the life of the track components resulting in shorter maintenance cycles. It is known that reducing variations in track modulus at grade (i.e. road) crossings leads to better track performance and less track maintenance. Ride quality, as indicated by vertical acceleration, is also strongly dependent on track modulus.

The economic constraints of both passenger and freight rail service are moving the industry to higher-speed rail vehicles and the performance of high-speed trains are likewise strongly dependent on track modulus. At high speeds, there is an increase in track deflection caused by larger dynamic forces. These forces become significant as rail vehicles reach 50 km/hr (30 mph) and rail deflections increase with higher vehicle speeds up to a critical speed. It is suggested that track with a high and consistent modulus will allow for higher train speeds and therefore increased performance and revenue.

Previous localized field-testing has shown that it is possible to measure areas of low-track modulus, variable-track modulus, void deflection, variable total deflection, and inconsistent rail deflection. In the past, these known systems have been used to identify sections of track with poor performance. Although these measurements are useful; they are expensive and only are made over short distances (~tens of meters). The ability to make these measurements continuously over large sections of track is desirable.

Previous vertical track modulus measurement systems can be placed in two categories: 1) trackside measurements, and 2) on-board measurements. With the trackside approach, a section of track is closed to rail traffic and a work crew uses specialized equipment to make measurements at various discrete locations.

In all trackside methods, rail deflection is measured before and after a static "point" load is applied. Differences lie in the number of deflection measurements made and how those measurements are used to estimate track modulus. Common trackside approaches include the Beam on Elastic Foundation method and the Deflection Basin method.

The Beam on an Elastic Foundation method uses a structural model, known as the Winkler Model, to represent the track system. The Winkler model represents a point load applied to an infinite Bernoulli beam on an infinite elastic foundation Trackside measurements of the deflection at the point where the load is applied are taken for a known load and modulus can then be calculated using:

$$u = \frac{1}{4}\left(\frac{1}{EI}\right)^{\frac{1}{3}}\left(\frac{P}{w_0}\right)^{\frac{4}{3}} \qquad (1)$$

where:
  u is the track modulus
  E is the modulus of elasticity of the rail
  I is the moment of inertia of the rail
  P is the load applied to the track
  $w_0$ is the deflection of the rail at the loading point This method only requires a single measurement and it has been suggested to be the best method for field measurement of track modulus. Its major limitation is that it provides only information for a single point along the rail. In reality, the modulus may be very different only a meter away. Also, if multiple loads are present. as with multi-axle railway vehicles used to apply the point load, small deflections must be assumed and superposition is needed. In this case the Winkler model cannot be simplified as in Equation (1) and an iterative solution is required. Also, slack in the rail can cause non-linearity in the load/deflection relationship. Therefore, a small load should be applied to determine the zero displacement position for the measurement. A heavy load is then applied and used as the loaded measurement. This further complicates this technique.

The second trackside technique, the Deflection Basin Method, uses the vertical equilibrium of the loaded rail to determine track modulus. In this approach rail deflection caused by a point load(s) is measured at several (ideally infinite) locations along the rail and the entire deflected "area" calculated. Using a force balance this deflected area, or deflection basin, can be shown to be proportional to the integral of the rail deflection:

$$P = \int_{-\infty}^{\infty} q(x)\,dx = \int_{-\infty}^{\infty} u\delta(x)\,dx = uA_\delta \qquad (2)$$

where:
  P is the load on the track
  q(x) is the vertical supporting force per unit length
  u is the track modulus
  δ(x) is the vertical rail deflection
  $A_\delta$ is the deflection basin area (area between the original and deflected rail positions)
  x is the longitudinal distance along the track The multiple deflection measurements required for this method result in longer traffic delays. Once again, both heavy and light loads are used to eliminate slack, which further increase the delays.

Both of these methods are time consuming and expensive and all suffer from the major limitation that the measured modulus is only valid along a small length of track. It is desirable to have a moving, i.e., on-board, modulus measurement system.

On-board measurements are made from a moving railcar and are more desirable because they can be made with less interruption of rail traffic and over longer distances. On-board measurements, however, are difficult because there is no stable reference frame. And, present on-board systems are labor intensive and move at slow speeds. Thus, they are limited to short distances (e.g. hundreds of meters) and still interrupt traffic. These previous systems use a long rigid truss that rides on two unloaded wheels. This truss creates a straight line, or cord, that is used as a reference for the measurement. A third wheel is then used to apply a load at midpoint of the cord (or truss) and the relative displacement between the loaded wheel and the unloaded truss is measured. The truss must be long enough, generally 30.48 m (100 ft), so that the two endpoints are not affected by the load at the center of the truss. This method again requires two measurements one with a light load, made with a similar truss, and the heavy load, to distinguish between changes in geometry and changes in modulus. The output of this approach is a measurement of the relative displacement of the loaded wheel with respect to the unloaded wheel and from this measurement the track modulus is then estimated.

One vehicle, called the Track Loading Vehicle (TLV), uses this approach. This vehicle is capable of measuring track modulus at speeds of 16.1 km/hr (10 mph). The TLV uses two cars, each with a center load bogie capable of applying loads from 4.45 kN to 267 kN (1 to 60 kips). A light load (13.3 kN or 3 kips) is applied by the first vehicle while a heavier load is applied by the second vehicle. A laser-based system on each vehicle measures the deflections of the rail caused by the center load bogies. The test procedure involves two passes over a section of track-first applying a 44.5 kN (10 kip) load and then a 178 kN (40 kip) load. The TLV still has limitations. First, tests are often performed at speeds below 16.1 km/hr (10 mph) so it is difficult to test long section of track (hundreds of miles). Second, significant expense in both equipment and personnel are required for operation. For these reasons the TLV has not yet been widely implemented.

Thus it is desirable to have an apparatus and method to determine track modulus from a moving railcar that is inexpensive, does not require significant support equipment, operates at higher speeds and could potentially be automated.

SUMMARY OF THE INVENTION

The present invention is directed to a system for measuring the relative displacement of a railroad track for determining the quality of the track and for use in determining vertical track modulus and vertical track stiffness. The system comprises a rail vehicle having a rail body and a set of wheels. Each wheel engages the rail at a wheel and rail contact point. The system further comprises a mechanism for measuring the vertical displacement of the track at a distance along the rail spaced from at least one of the wheel and rail contact points and a mechanism for recording the vertical displacement of the track as the vehicle travels along the rail.

In accordance with another embodiment of the present invention, a noncontact method for measuring the performance of a portion of railroad track as a rail vehicle travels along the rail is disclosed. The method comprises the steps of measuring the relative displacement of the portion of track from a rail vehicle at a distance spaced from a wheel and rail contact point as the rail vehicle is moving along the track and calculating one of the vertical track modulus and vertical track stiffness from the relative displacement.

BRIEF DESCRIPTION OF THE SEVERAL VIEWS OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DETAILED DESCRIPTION OF THE INVENTION

Figure 1:
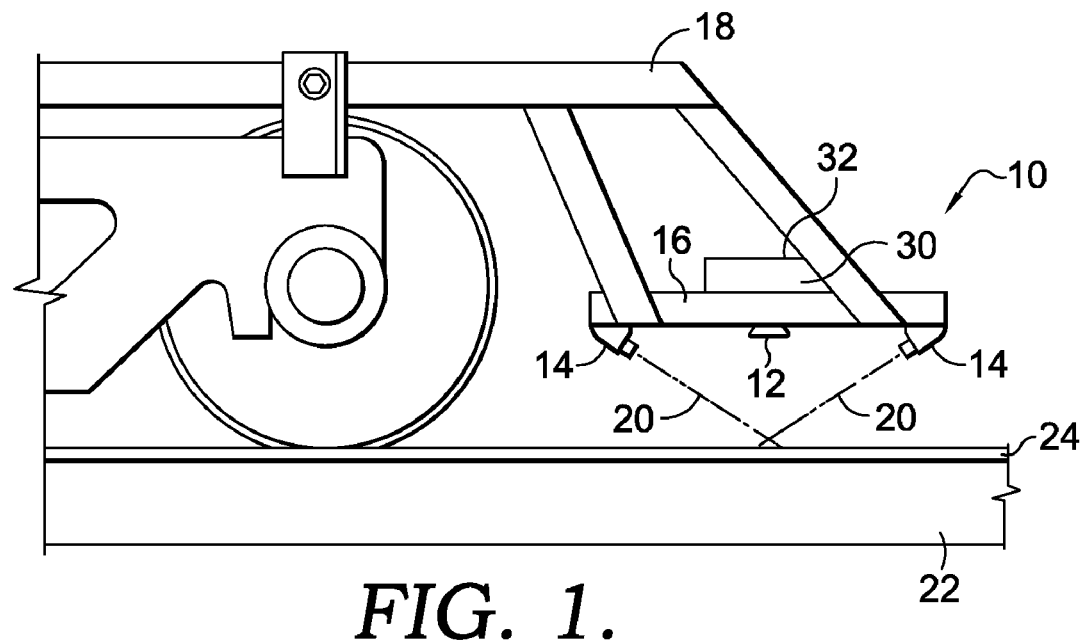
FIG. 1 is a schematic of the modulus measurement system mounted to a train showing an exemplary embodiment of the present invention.

FIG. 1 illustrates the on-board, noncontact measurement system 10 of the present invention. The system 10 measures vertical track displacement relative to the wheel-and-rail contact point and these relative measurements are combined with an analytical model of the track structure and the measured vehicle loads (weight and dynamic forces) to estimate the vertical track modulus and track stiffness for the track. Vertical track stiffness is the ratio of applied load to displacement and includes the effects from rail, subgrade, ballast, subballast, ties, and fasteners. Vertical track modulus generally does not include the effects of the rail.

Figure 3:
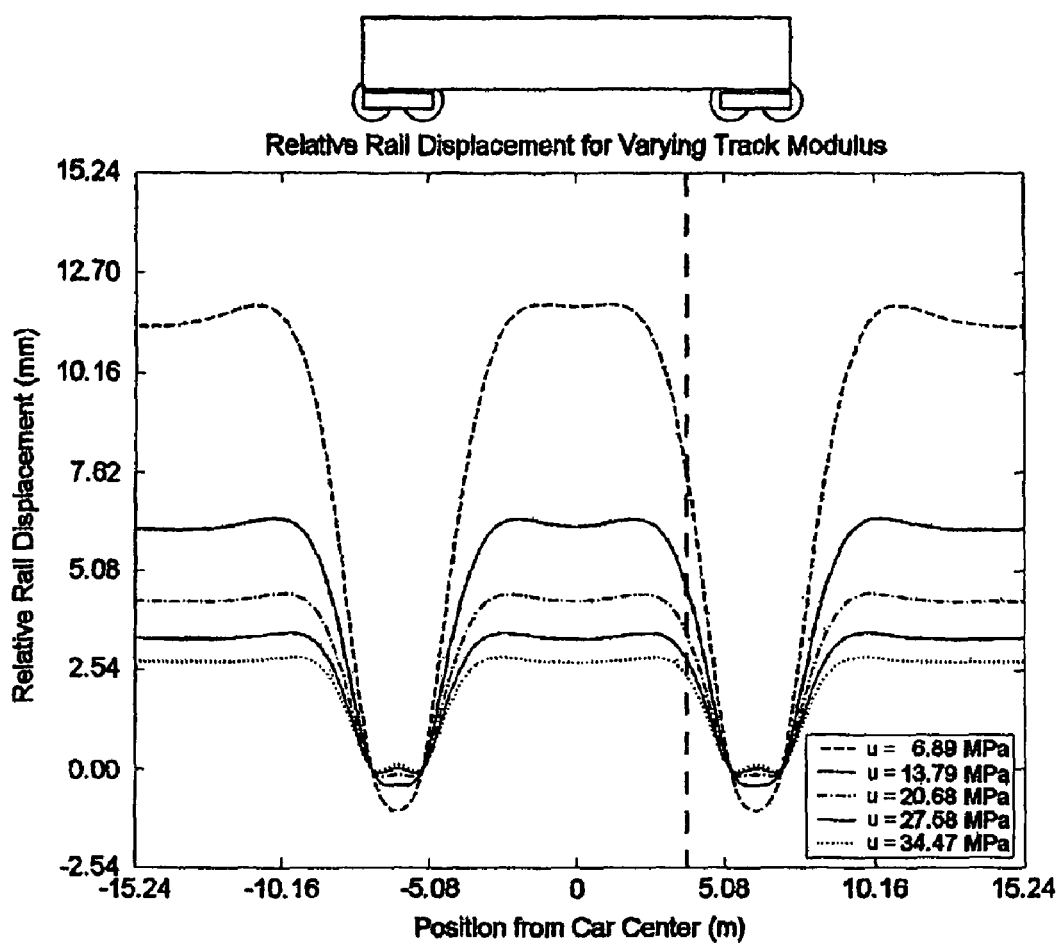
FIG. 3 is a diagram of relative rail displacement showing varying rail modulus for varying distances from the train center.

The system 10 comprises a digital vision system 12, a means for measuring the vertical distance between a position on the rail vehicle and the upper surface of the rail 14, and a data processor (not shown). The digital vision system is preferably a digital video camera having a storage device for recording the images. As shown in FIG. 1, the camera 12 is mounted to the railroad truck on a bracket 16 mounted to a side frame of the rail truck 18. The camera 12 preferably extends rearwardly between approximately 1 and 2 meters toward the center of the car relative to the wheel/rail contact point, as shown in FIG. 3. Most preferably, the camera extends approximately 1.25 m (48 in.).

The means for measuring the vertical distance from the rail vehicle to the upper surface of the rail may comprise optical emitters 14. Preferably two line lasers or other suitable devices are used to provide a beam in the visible spectrum. The line lasers 14 are rigidly attached to the bracket 16 such that the camera and lasers are substantially coaxially aligned. The digital camera 12 is mounted between the line lasers. The emitters and camera are mounted such that the vertical distance between each of the emitters and camera and the wheel and rail contact point is substantially constant. The lasers are mounted such that the each laser beam 20 is projected at an acute angle (~30°) relative to the bracket or side rail of the truck and will project onto the rail head. It is to be understood that the line lasers may project at other angles, but that each laser must project at the same angle as the other laser. It is further to be understood that the means for measuring the vertical distance between the rail vehicle and the upper surface of the rail may comprise laser interferometers or other know methods of measurement.

Figure 2:
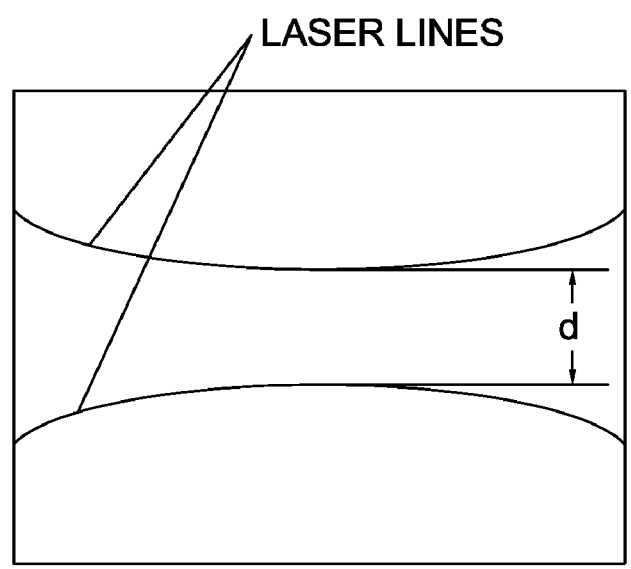
FIG. 2 is a diagram illustrating the beams of light as they appear on the rail.

As shown in FIG. 2, the projected laser beam 20 provides a substantially arcuate profile across the surface of the rail because of the curved profile of the rail head 24 across the surface of the rail 22. The camera 12 of the sensor system 10 observes and records the distance between the two laser lines, d. On softer track, the rail 22 will rise relative to the wheel/rail contact point and the laser lines as observed by the camera will move closer together. Conversely, the distance between the lasers will increase on stiffer track. Using line lasers 14 allows the system to compensate for lateral movement of the rail 22 relative to the camera 12 and for changes in rail 10 profile. These changes in rail profile may occur over time for the same piece of rail or along the rail as the vehicle moves. The use of line lasers are particularly helpful in accommodating these changes in rail head profile.

Figure 4:
FIG. 4 is an image from the camera of the present invention illustrating the beams of light on the rail and the odometer readings associated with the image.

In order to locate the measurements to the track, an odometer 26 is provided. The odometer 26 is mounted such that it is observed and its measurements recorded by the camera adjacent the line profiles, as shown in FIG. 4. The odometer 26 locates the measurements along the track. In addition or alternatively, automatic image geocoding may be used to attach GPS localization to the images. The automatic image geocoding may be done through a GPS receiver plug-in (not shown) for the camera. The date, time and GPS stamps are permanent, non-modifiable, intrinsic information that is attached as pixels into the digital images The video images are recorded and post processed by a processor 30 coupled to a memory 32. The processor 30 may represent one or more processors (e.g., microprocessors), and the memory 32 may represent the random access memory (RAM) devices comprising the main storage of the respective computer, as well as any supplemental levels of memory, e.g., cache memories, non-volatile or backup memories (e.g., programmable or flash memories), read-only memories, etc. In addition, each memory 32 may be considered to include memory storage physically located elsewhere in a respective computer, e.g., any cache memory, or any storage capacity used as a virtual memory such as in a mass storage device.

The processor 30 operates under the control of an operating system, and executes or otherwise relies upon various computer software applications, components, programs, objects, modules, data structures, etc. Two steps must be performed in the video processing. The first is determining which part of the image is a part of either of the first or second laser curves associated with the first and second lasers, respectively. The lasers are isolated using color filtering and threshold algorithms. Edge detecting algorithms were then used to locate the positions of the laser curves in the image. Preferably, the curve of each laser is fitted with a second order polynomial. Finally, the minimum distance between these two polynomials is found analytically. Using a curve-fitting polynomial makes the system robust to small variations in rail head profile.

The computer then uses a mathematical model to calculate the track modulus from the minimum distance d between the lasers. Three mathematical planar models of rail deflection are presented herein. The first is the widely accepted Winkler model, the second is a discrete support (crosstie) model used to estimate track modulus, and the third is a nonlinear stiffness model. These models all assume knowledge of the rail's elastic modulus and cross-sectional geometry which are commonly available for all commercial rail.

The Winkler model describes the deflection of an infinitely long beam resting on an infinite continuous, uniform, elastic foundation in response to a single point load. In this model the deflection of the beam under an applied load is linearly proportional to the pressure between the base of the rail and the foundation. This model has been shown to be an effective method for determining track modulus. The vertical deflection of the rail, y, as a function of longitudinal distance along the rail x (referenced from the applied load) is given by:

$$y(x) = -\frac{P\beta}{2u}e^{-\beta x}[\cos(\beta x) + \sin(\beta x)] \quad (7)$$

where:

$$\beta = \left(\frac{u}{4EI_z}\right)^{\frac{1}{4}} \quad (8)$$

where:
P is the load on the track
u is the track modulus
E is the modulus of elasticity of the rail.
$I_z$ is the moment of inertia of the rail.
x is the longitudinal distance along the rail When multiple loads are present the rail deflections caused by each of the loads are superposed (assuming small vertical deflections).

A plot of the rail deflection given by the Winkler model over the length of a four-axle coal hopper is shown in FIG. 3.

The deflection is shown relative to the wheel/rail contact point for five different reasonable values of track modulus (6.89, 13.8, 20.7, 27.6, and 34.5 MPa or 1000, 2000, 3000, 4000, and 5000 lbf/in/in). The model assumes a 115 lb rail with an elastic modulus of 206.8 GPa (30,000,000 psi) and an area moment of inertia of 2704 cm$^4$ (64.97 in$^4$). FIG. 3 shows larger rail displacements with respect to the wheel/rail contact point occur with low track modulus.

A first alternative model is the discrete support model, which describes the rail supported on a number of discrete springs with a single force applied. The discrete model is preferred over the Winkler model because of its additional ability to represent non-uniform track. In this model, the discrete springs represent support at the crossties and the single applied load represents one railcar wheel. Tie support is modeled by linearly elastic springs. The proposed model considers only finite lengths of rail and a finite number of ties. To reduce the model's computational requirements (so it can be implemented in real time) the rail is assumed to extend beyond the ties and is fixed at a (large) distance from the last tie. This ensures the boundary conditions are well defined (i.e., the rail is flat far away) and the rail shape is continuous.

The deflection in each of the springs (i.e. the rail deflection) can be determined by first solving for the forces in each of the springs using energy methods The principles of stationary potential energy and Castigliano's theorem on deflections are applied. For these methods to be applicable small displacements and linear elastic behavior is assumed. The number of equations needed to determine the forces in the springs is equal to the number of springs (i.e. spring forces are the unknowns).

The discrete support model is similar to the Winkler model when the ties are uniformly spaced, have uniform stiffness, and the rail is long. The moment and shear force in the cantilevered sections of the model can be calculated. Static equilibrium requires the moment and shear force, for Section A in FIG. 5, to be:

$$M_1 = M_A + V_A x_1 \quad (9)$$

$$V_1 = V_A \quad (10)$$

Likewise, for Section C:

$$M_2 = M_C + V_C x_2 \quad (11)$$

$$V_2 = V_C \quad (12)$$

Figure 5:
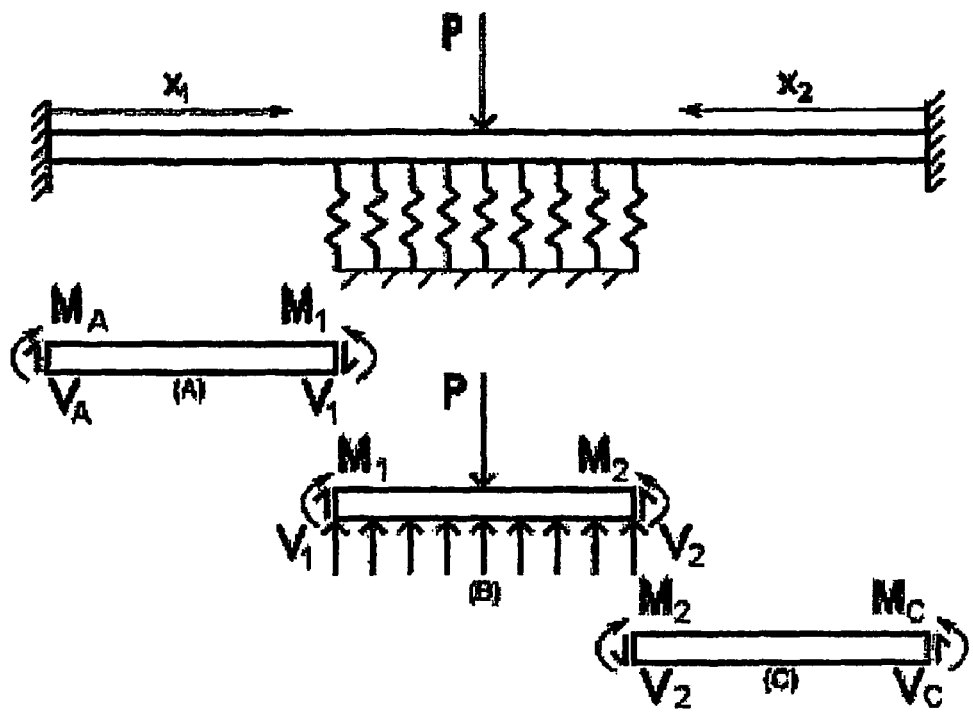
FIG. 5 is an illustration of the moments for the discrete support model of the present invention.
Figure 6:
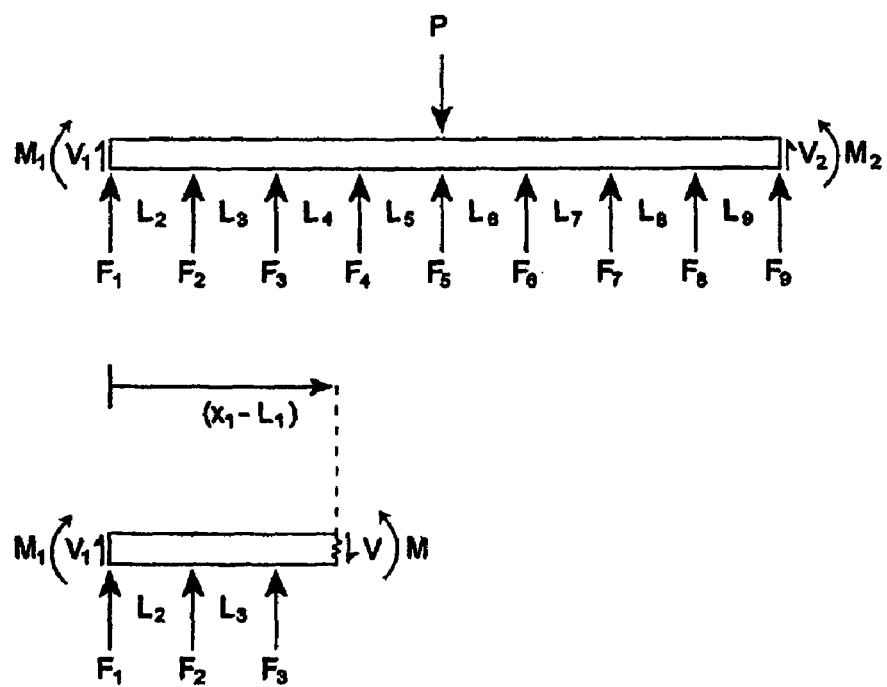
FIG. 6 is an illustration of the internal beam moments for the discrete support model of the present invention.
Figure 7:
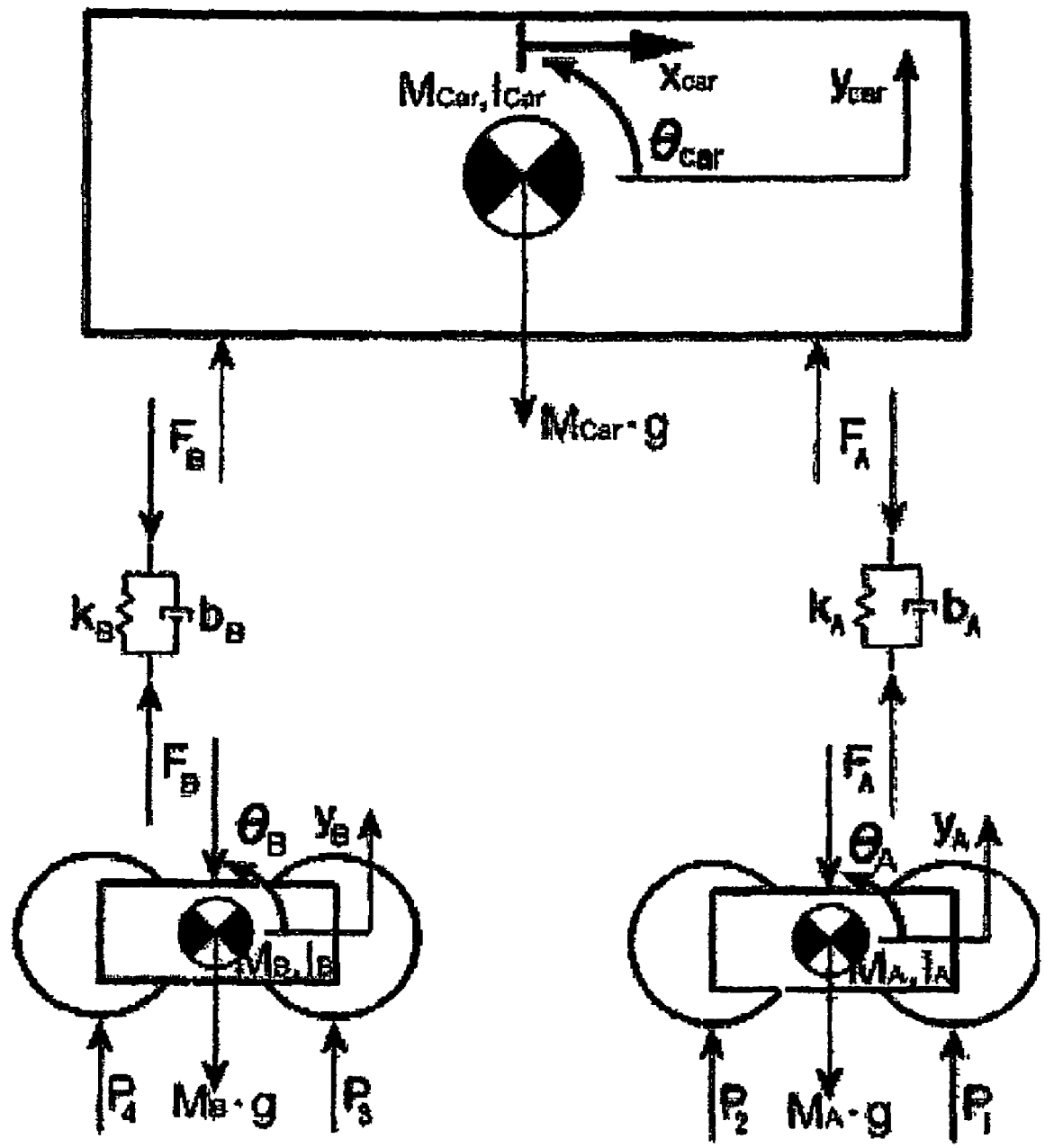
FIG. 7 is an illustration of the dynamic interaction between the railcar and the track for the discrete support model of the present invention.

Now, the forces in the springs can be determined with energy methods. Section B of FIG. 5 is split into segments separated by the springs and the segment's internal moments are found (as in Eqs. 9 and 11 above) to determine the beam's strain energy from the internal moments, as shown in FIG. 7. Energy from shear force is small and is neglected.

The equations for the internal moments in each segment can be written, Eqs. (13)-(22), where moments $M_1$ and $M_2$, and the shear forces $V_1$ and $V_2$ are given by equations 9-12. The lengths of each of the segments (i.e. tie spacing) in the beam are given by $L_1$-$L_{10}$ and the spring forces are denoted by $F_1$-$F_9$ (FIG. 7).

$$M = M_1 \quad (13)$$
for $0 \le x_1 \le L_1$ $$M = -[M_1 + V_1(x_1 - L_1) + F_1(x_1 - L_1)] \quad (14)$$
for $L_1 \le x_1 \le L_1 + L_2$ $$M = -[M_1 + V_1(x_1 - L_1) + F_1(x_1 - L_1) + F_2(x_1 - L_1 - L_2)] \quad (15)$$
for $L_1 + L_2 \le x_1 \le L_1 + L_2 + L_3$ $$M = -\begin{bmatrix} M_1 + V_1(x_1 - L_1) + F_1(x_1 - L_1) + \\ F_2(x_1 - L_1 - L_2) + F_3(x_1 - L_1 - L_2 - L_3) \end{bmatrix} \quad (16)$$
for $L_1 + L_2 + L_3 \le x_1 \le L_1 + L_2 + L_3 + L_4$ $$M = -\begin{bmatrix} M_1 + V_1(x_1 - L_1) + F_1(x_1 - L_1) + F_2(x_1 - L_1 - L_2) + \\ F_3(x_1 - L_1 - L_2 - L_3) + F_4(x_1 - L_1 - L_2 - L_3 - L_4) \end{bmatrix} \quad (17)$$
for $L_1 + L_2 + L_3 + L_4 \le x_1 \le L_1 + L_2 + L_3 + L_4 + L_5$ $$M = \begin{bmatrix} M_2 + V_2(x_2 - L_{10}) + F_9(x_2 - L_{10}) + F_8(x_2 - L_{10} - L_9) + \\ F_7(x_2 - L_{10} - L_9 - L_8) + F_6(x_2 - L_{10} - L_9 - L_8 - L_7) \end{bmatrix} \quad (18)$$
for $L_{10} + L_9 + L_8 + L_7 \le x_2 \le L_{10} + L_9 + L_8 + L_7 + L_6$ $$M = \begin{bmatrix} M_2 + V_2(x_2 - L_{10}) + F_9(x_2 - L_{10}) + \\ F_8(x_2 - L_{10} - L_9) + F_7(x_2 - L_{10} - L_9 - L_8) \end{bmatrix} \quad (19)$$
for $L_{10} + L_9 + L_8 \le x_2 \le L_{10} + L_9 + L_8 + L_7$ $$M = [M_2 + V_2(x_2 - L_{10}) + F_9(x_2 - L_{10}) + F_8(x_2 - L_{10} - L_9)] \quad (20)$$
for $L_{10} + L_9 \le x_2 \le L_{10} + L_9 + L_8$ $$M = [M_2 + V_2(x_2 - L_{10}) + F_9(x_2 - L_{10})] \quad (21)$$
for $L_{10} \le x_2 \le L_{10} + L_9$ $$M = -M_2 \quad (22)$$
for $0 \le x_2 \le L_{10}$ In the above equations, the shear forces, moments, and spring forces are all unknown, however, one spring force can be determined by a vertical force balance:

$$F_1 = P - V_1 - V_2 - F_2 - F_3 - F_4 - F_5 - F_6 - F_7 - F_8 - F_9 \quad (23)$$

where P is a known wheel load (e.g. 157 kN or 35 kips). Now, the strain energy can be written where $k_i$ is the stiffness of spring i:

$$U = \int_0^{L_1} \frac{M^2}{2EI} dx_1 + \int_{L_1}^{L_1+L_2} \frac{M^2}{2EI} dx_1 + \int_{L_1+L_2}^{L_1+L_2+L_3} \frac{M^2}{2EI} dx_1 + \\ \int_{L_1+L_2+L_3}^{L_1+L_2+L_3+L_4} \frac{M^2}{2EI} dx_1 + \int_{L_1+L_2+L_3+L_4}^{L_1+L_2+L_3+L_4+L_5} \frac{M^2}{2EI} dx_1 + \\ \int_0^{L_{10}} \frac{M^2}{2EI} dx_2 + \int_{L_{10}}^{L_{10}+L_9} \frac{M^2}{2EI} dx_2 + \int_{L_{10}+L_9}^{L_{10}+L_9+L_8} \frac{M^2}{2EI} dx_2 + \\ \int_{L_{10}+L_9+L_8}^{L_{10}+L_9+L_8+L_7} \frac{M^2}{2EI} dx_2 + \int_{L_{10}+L_9+L_8+L_7}^{L_{10}+L_9+L_8+L_7+L_6} \frac{M^2}{2EI} dx_2 + \\ \frac{F_1^2}{2k_1} + \frac{F_2^2}{2k_2} + \frac{F_3^2}{2k_3} + \frac{F_4^2}{2k_4} + \frac{F_5^2}{2k_5} + \frac{F_6^2}{2k_6} + \frac{F_7^2}{2k_7} + \frac{F_8^2}{2k_8} + \frac{F_9^2}{2k_9} \quad (24)$$

Castigliano's theorem is now used to create the number of equations needed to solve for the unknown spring forces and boundary conditions (moment and shear force). In this case, there are 12 unknown variables (8 spring forces, 2 reaction moments, and 2 reaction forces). From Castigliano's theorem:

$$\frac{\partial Y}{\partial F_2} = \quad (25)$$

$$\frac{\partial U}{\partial F_3} = \frac{\partial U}{\partial F_4} = \frac{\partial U}{\partial F_5} = \frac{\partial U}{\partial F_6} = \frac{\partial U}{\partial F_7} = \frac{\partial U}{\partial F_8} = \frac{\partial U}{\partial F_9} = 0,$$

$$\frac{\partial U}{\partial M_A} = \frac{\partial U}{\partial M_B} = 0, \text{ and } \frac{\partial U}{\partial V_A} = \frac{\partial U}{\partial V_B} = 0$$

With these relationships a set of 12 equations and 12 unknowns is developed by substituting the moment expressions (Eqs. 9-23) into (Eq. 24). These expressions can be written in matrix form:

$$MF = P \quad (26)$$

where:

P is the load vector

M is a 12×12 matrix of coefficients of the external forces

Figure 8:
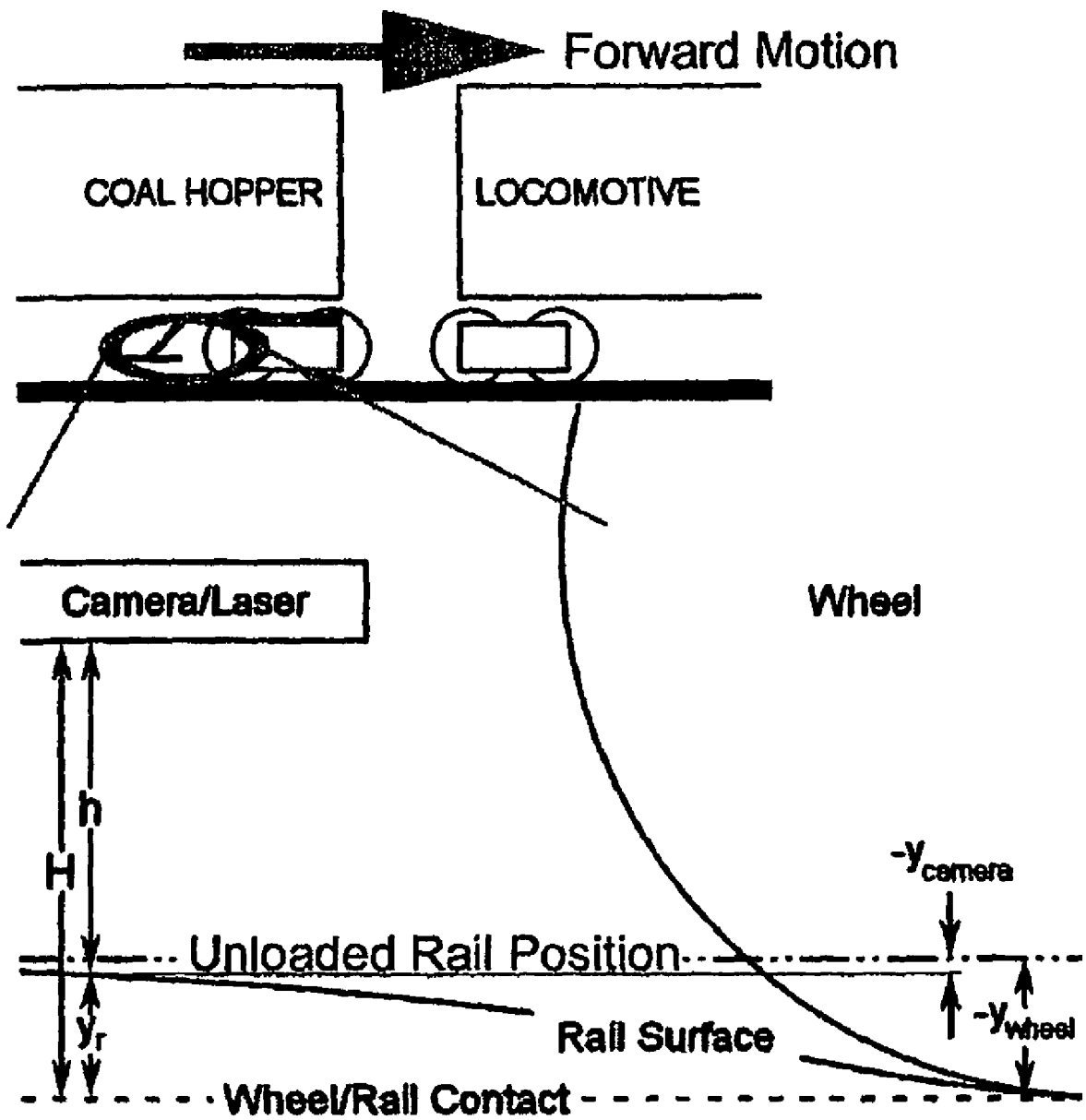
FIG. 8 is an illustration of the kinematics of the sensor system for the discrete support model of the present invention.

F is a column vector of the external forces $F_2$-$F_9$, $M_A$, $V_A$, $M_B$, and $V_B$ The solution to this matrix equation gives the forces in each of the springs. Now, the spring deflections are:

$$d_i = \frac{F_i}{k_i} \quad (27)$$

where:

$d_i$ is the deflection of spring i $F_i$ is the force in spring i $k_i$ is the stiffness of spring i Along with the track model, a planar railcar model must be used to predict the performance of the sensor system 10 of the present invention. This model must allow for horizontal (x) and vertical (y) motion as well as planar rotation of the car body and both trucks. The car body and both trucks each have an associated mass and the car body is separated from each truck by a spring/damper suspension system, as shown in FIG. 8. The model represents dynamic interaction between the railcar and the track model presented in the previous section through the wheel contact loads ($P_1$-$P_4$). Changes in track modulus or changes in track geometry will cause changes in dynamic loading at each wheel.

The equations of motion can now be written for the car body:

$$F_A + F_B - M_{car}g = M_{car}\ddot{y}_{car} \quad (28)$$

$$F_A L - F_B L = I_{car}\ddot{\theta}_{car} \quad (29)$$

and for each truck (assuming small angles):

$$P_1 + P_2 - F_A - M_A g = M_A \ddot{y}_A \quad (30)$$

$$P_1 l - P_2 l = I_A \ddot{\theta}_A \quad (31)$$

$$P_3 + P_4 - F_B - M_B g = M_B \ddot{y}_B \quad (32)$$

$$P_3 l - P_4 l = I_B \ddot{\theta}_B \quad (33)$$

In the above equations, L is the distance between the car body center and truck center. The distance between each wheel and the truck center is l.

Next, expressions for the forces $F_A$ and $F_B$ can be determined from the free body diagrams for the suspension system (spring and dampers):

$$F_A = k_A(y_A - y_{car} - L\sin\theta_{car}) + b_A(\dot{y}_A - \dot{y}_{car} - L\sin\theta_{car}) \quad (34)$$

$$F_B = k_B(y_B - y_{car} + L\sin\theta_{car}) + b_B(\dot{y}_B - \dot{y}_{car} + L\sin\theta_{car}) \quad (35)$$

The horizontal motion is considered an input derived from the train velocity and it is assumed that each wheel maintains rail contact. Therefore, the angle of each truck is related to the displacement of its wheels. For Truck A the relationship is:

$$y_A = \frac{y_1 + y_2}{2} \quad (36)$$

$$\sin\theta_A = \frac{y_1 - y_2}{2l} \quad (37)$$

where each $y_i$ corresponds to the displacement at the wheel contact points (e.g., $y_1$ corresponds to the displacements at load $P_1$) and l is the length of the truck. The deflection of the wheels can then be shown to be:

$$y_1 = y_A + l\theta_A \quad (38)$$

$$y_2 = y_A - l\theta_A \quad (39)$$

Now wheel displacements are expressed in terms of truck displacements and angles.

Also, since the trucks are far apart and the rotation of the car body is small it is assumed there is no interaction between the wheel loads at Truck A and Truck B (however, there can be interaction from the left to the right rail for a given truck). Therefore, if the Winkler model (Equation 7) is used and the deflections are superposed, the deflection at wheels 1 and 2 of Truck A are:

$$y_1 = \frac{P_1 \beta_1}{2u_1} + \frac{P_2 \beta_2}{2u_2}\alpha_2 \quad (40)$$

$$y_2 = \frac{P_2 \beta_2}{2u_2} + \frac{P_1 \beta_1}{2u_1}\alpha_1 \quad (41)$$

where:

$$\alpha_1 = e^{-\beta_1 x}(\cos\beta_1 x + \sin\beta_1 x) \quad (42)$$

$$\alpha_2 = e^{-\beta_2 x}(\cos\beta_2 x + \sin\beta_2 x) \quad (43)$$

Equations 40 and 41 determine the deflections at each of the applied loads, $P_1$ and $P_2$. These equations are the result of using the Winkler model (Eq. 7) and superposition of both loads.

Finally, the wheel contact forces ($P_1 \ldots P_4$) are determined are determined assuming a quasi-static interaction with the rail:

$$P_1 = \frac{2u_1}{\beta_1}\frac{y_1 - \alpha_2 y_2}{1 + \alpha_1 \alpha_2} \quad (44)$$

$$P_2 = \frac{2u_2}{\beta_2}\frac{y_2 - \alpha_1 y_1}{1 + \alpha_1 \alpha_2} \quad (45)$$

The track and car models above are used with a model of the sensor system to emulate the measurement system. The sensor model is a kinematic relationship between the sensors and rail. FIG. 8 shows the kinematics of the sensor system. It is assumed that the sensor system is rigid with respect to the wheel contact point (H is constant). This is a reasonable assumption as the instrument beam, truck, and wheels are all massive, nearly rigid elements and these elements do not include the suspension of the railcar. Rotation of the side frame ($\theta_A$) could cause this distance (H) to change but this rotation has been experimentally shown to be insignificant. The height between the sensor system and the wheel contact point (H) is needed for calibration of the system and this can be accomplished by taking measurements over a location of known modulus.

The sensor system 10 measures the distance between the camera image plane and the rail surface, h. Then, the displacement of the rail surface with respect to the wheel/rail contact plane, $y_r$ ($y_r$=H–h) can be found. The displacement, $y_r$, can then be related to the absolute rail deflection (with respect to the undeflected/unloaded rail), $y_{camera}$, and the absolute deflection of the wheel/rail contact point, $y_{wheel}$ ($y_r=y_{camera}-y_{wheel}$)

Figure 9:
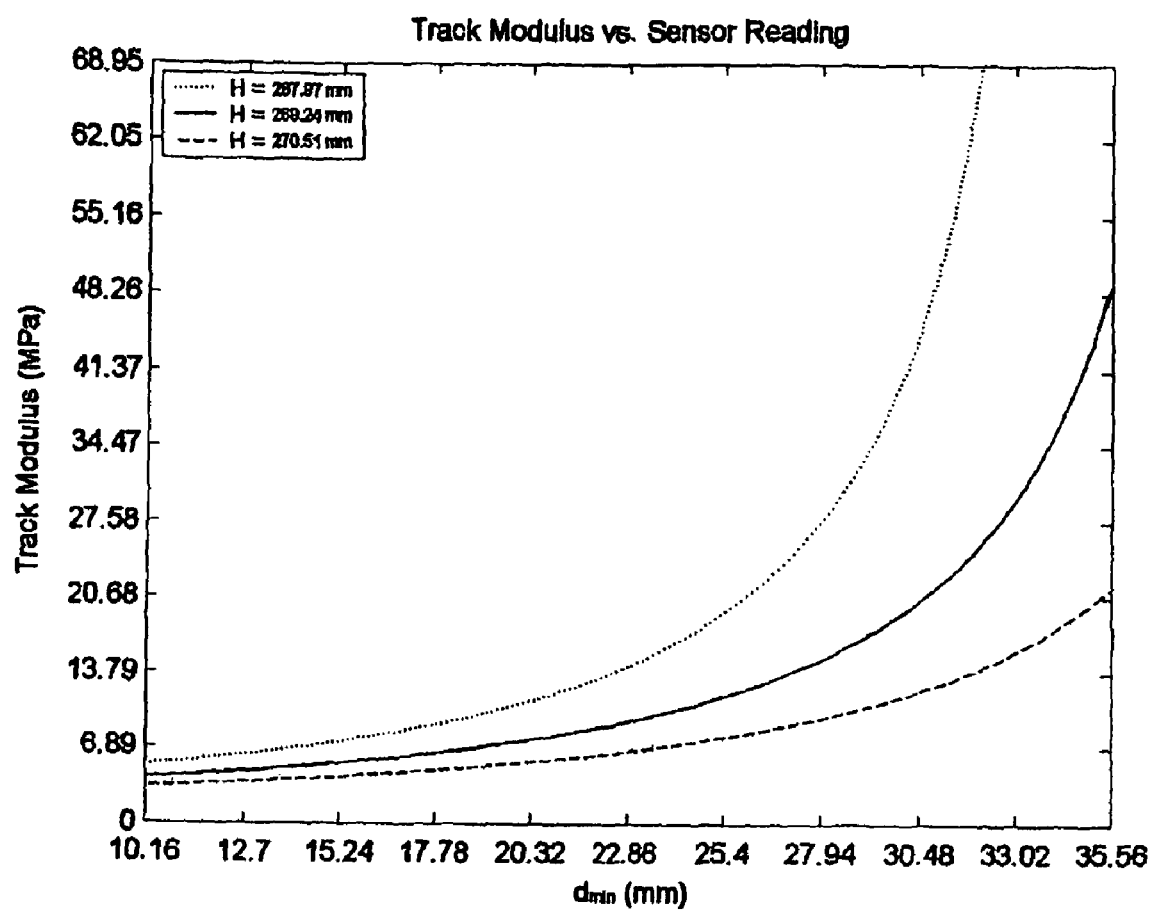
FIG. 9 is a diagram illustrating the track modulus for three different distances between the camera image plane and the wheel/rail contact point.

As shown in FIG. 9, the height of the sensor system above the rail (h) can now be related to the sensor reading (d) through the following geometry:

$$(L_1+l_1)\tan\theta_1 = h \qquad (49)$$

$$(L_2+l_2)\tan\theta_2 = h \qquad (50)$$

$$d = l_1 + l_2 \qquad (51)$$

where:

$L_1$, $L_2$=horizontal position of the lasers from the camera $\theta_1$ and $\theta_2$ are the angles between the lasers and the horizontal $l_1$, $l_2$=the distances from the camera's centerline and the rail/laser intersection Substituting (49) and (50) into (51) gives (d):

$$d = \frac{h}{\tan\theta_1} + \frac{h}{\tan\theta_2} - (L_1 + L_2) \qquad (52)$$

Figure 10:
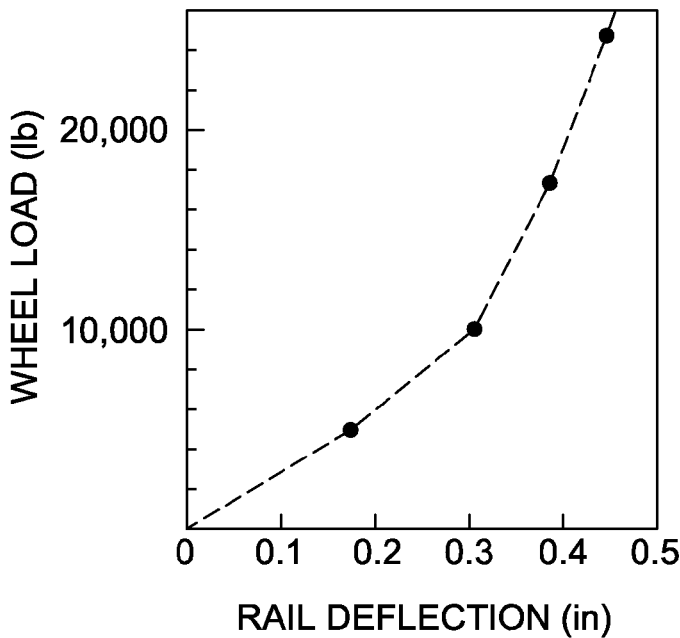
FIG. 10 is a diagram illustrating the relationship between wheel load and track deflection.

Combining this information with the track model (e.g. Winkler model (Eq. 7)), the sensor reading (d) can be related to the track modulus (u). The relationship is nonlinear because of the nonlinear track model. FIG. 10 shows curves for the system for three different distances between the camera image plane and the wheel/rail contact point (H). Changing this distance shifts the curve and changes the system's sensitivity. Therefore, the sensor system should be mounted at a height (H) that is appropriate for the type of track to be measured. This parameter (H) must be found to calibrate the system using trackside measurements.

A second alternative model is the nonlinear stiffness model. For nearly a century it has been well known that the overall track stiffness is a nonlinear function that relates applied load to track deflection. The relationship between wheel load and track deflection is as shown in FIG. 10. This curve represents the behavior of real track and is clearly nonlinear.

The standard track-deflection solution is based on the beam on an elastic foundation equation $$EI\frac{d^4w}{dx^4} + p(x) = 0 \qquad (53)$$

where:

$p(x)=kw$ is the rail support pressure w is the rail deflection k is a linear spring constant The constant k in the rail support pressure relates the deflection of the rail (w) to support pressure. This constant is determined experimentally by plotting the rail support pressure against the rail deflection (see FIG. 11) and finding the slope k of the linearized line. The resulting solution is, therefore, only a rough approximation to the actual behavior of the loaded track.

Figure 11:
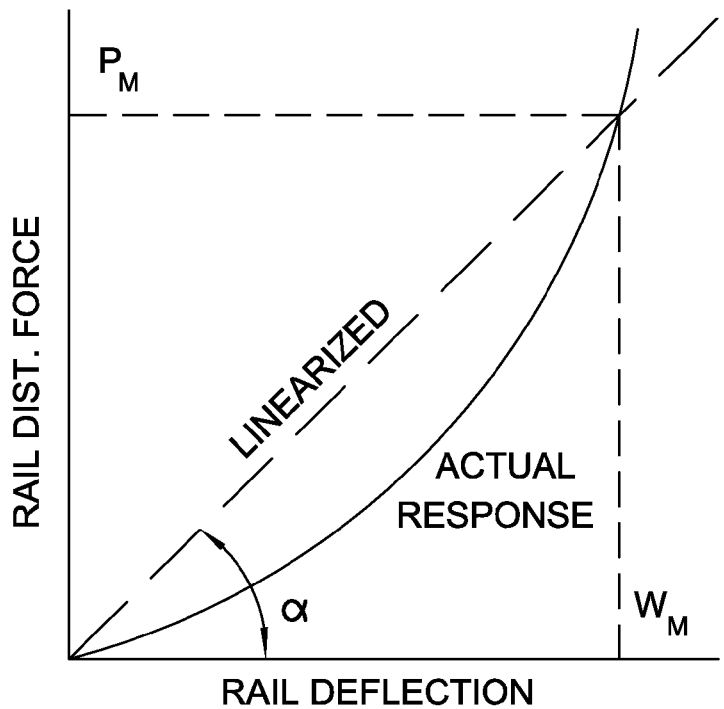
FIG. 11 is a diagram illustrating the relationship between rail distribution force and rail deflection.

To more closely approximate the curve of FIG. 11 a nonlinear form $$p(x) = k_1 w + k_3 w^3 \qquad (54)$$

has been proposed in this work for the rail support pressure. This nonlinear form replaces kw in equation to define a new governing differential equation $$EI\frac{d^4w}{dx^4} + k_1 w + k_3 w^3 = 0 \qquad (55)$$

In addition, the boundary condition, equation (2), must be replaced by $$P = \int_{-\infty}^{\infty}(k_1 w + k_3 w^3)dx \qquad (56)$$

This boundary condition states that the vertically applied pressure (p(x)) must balance the applied load (P). Several solutions to the above differential equation (equation 55 subjected boundary condition 56) can be put forth using various numerical and/or analytical techniques. One solution has been proposed to be, but is not limited to:

$$\beta_0 = \sqrt[4]{\frac{k_1}{4EI}} = \sqrt[4]{\frac{A_1}{4}} \qquad (57)$$

$$\beta_0^4 = \frac{k_1}{4EI} = \frac{A_1}{4} \qquad (58)$$

$$4\beta_0^4 = \frac{k_1}{EI} = A_1 \qquad (59)$$

$$4\beta^4 = 4\beta_0^4 + \mu b_1 \qquad (60)$$

$$b_1 = 4\beta^4 - 4\beta_0^4 \qquad (61)$$

$$b_1 = 4\beta^4 - \frac{k_1}{EI} \qquad (62)$$

-continued $$w = C_0 e^{-\beta x}\cos\left(\beta x - \frac{\pi}{4}\right) + \tag{63}$$

$$C_1 e^{-\beta x}\cos\left(\beta x - \frac{\pi}{4}\right) + \left[4\beta^4 - \frac{k_1}{EI}\right]\frac{C_0 e^{-\beta x}}{16\beta^4}$$

$$[\sin\beta x + 2\beta x\sin\beta x] + \left[4\beta^4 - \frac{k_1}{EI}\right]\frac{C_0 x e^{-\beta x}}{8\beta^3}[\sin\beta x] -$$

$$\frac{A_3 C_0^3 e^{-3\beta x}}{\beta^4}\left\{\begin{array}{c}\cos\beta x\sin 2\beta x - \frac{\cos\beta x\cos 2\beta x}{32} + \frac{\cos\beta x\cos 4\beta x}{80} + \\ \left[\begin{array}{c}\sin\beta x\cos\beta x + \\ -\frac{7\sin\beta x}{80} - \frac{\sin\beta x\sin 2\beta x}{16} - \\ \frac{\sin 2\beta_4}{80}\left(\begin{array}{c}2\sin\beta x\cos 2\beta x + \\ \sin\beta x\sin 2\beta x\end{array}\right)\end{array}\right]\end{array}\right\}$$

subject to the boundary condition (56).

The modulus measurement system 10 of the present invention is able to measure the correct trend in track modulus, and is able to correctly resolve modulus changes from tie to tie. Further, the system 10 is able to consistently measure track modulus at train speeds up to 65 km/hr (40 mph) and to identify modulus variations between both rails.

It is to be understood that the specific embodiments of the present invention that are described herein is merely illustrative of certain applications of the principles of the present invention. It will be appreciated that, although an exemplary embodiment of the present invention has been described in detail for purposes of illustration, various modifications may be made without departing from the spirit and scope of the invention. Therefore, the invention is not to be limited except as by the appended claims.

What is claimed is:

1. A system for measuring the displacement of a portion of a railroad track relative to a wheel and rail contact point, the system comprising:
    a rail vehicle having a body comprising a substantially horizontal frame, and a set of wheels, one of the wheels of the set of wheels engaging the rail at the wheel and rail contact point;
    first and second optical emitters emitting first and second optical beams, the first and second optical emitters being mounted to the frame at an acute angle relative to the substantially horizontal frame of the body in spaced and opposed relation to each other such that the beams of the first and second optical emitters are converging as the beams are emitted from the first and second optical emitters, the first and second optical beams being detectable on an underlying surface and separated by a distance thereon; and
    a digital vision system mounted to the vehicle body for recording the first and second optical beams as they reflect from the underlying surface for measuring the vertical displacement of the track at a distance along the rail spaced from at least one of the wheel and rail contact points.

2. The system of claim 1 further comprising means for determining the vertical track modulus for the portion of the rail based on the vertical displacement of the track relative to the wheel and rail contact point for the portion of the track.

3. The system of claim 1 further comprising an odometer.

4. The system of claim 1 further comprising automatic image geocoding.

5. The system of claim 2 wherein the means for determining the vertical track modulus for a particular portion of the surface further comprises a processor.

6. The system of claim 5 wherein the processor includes software that runs a Winkler model to determine the track modulus for a particular portion of the track.

7. The system of claim 5 wherein the processor includes software that runs a discrete support model to determine the track modulus for a particular portion of the track.

8. The system of claim 5 wherein the processor includes software that runs a nonlinear track stiffness model to determine the track modulus for a particular portion of the track.

9. The system of claim 5 wherein the processor comprises storage and is configured to continuously register and calculate the relative rail deflection at the distance along the rail spaced from the at least one wheel and rail contact point.

10. The system of claim 1 wherein the distance along the rail spaced from the at least one wheel and rail contact point is approximately between 1 and 2 meters of the wheel-and-rail contact location.

11. The system of claim 1 wherein the distance along the rail for measuring the vertical displacement is spaced from the at least one wheel and rail contact point by approximately 1.25 meters toward the center of the car.

12. A noncontact method for measuring performance of a portion of railroad track, the method comprising the steps of: measuring the relative displacement of the portion of track from a rail vehicle at a distance spaced from a wheel and rail contact point as the rail vehicle is moving along the track by providing first and second spaced optical emitters each mounted to the rail vehicle at a specific acute angle and in opposed relation, the optical emitters being configured to emit first and second beams of light visible on the underlying rail surface and being separated by a distance thereon; and providing a camera mounted to the vehicle for recording the first and second beams of light as the rail vehicle travels along the surface.

13. The method of claim 12 further comprising the step of calculating one of the vertical track modulus and vertical track stiffness from the relative displacement.

14. The method of claim 1 further including the step of recording the location of the rail corresponding to the distance between the first and second beams of light.

15. The method of claim 14 further comprising the step of continuously measuring the minimum distance between the first and second beams of light by:
    determining the part of the image that is a part of either of the first or second beams of light associated with the first and second optical emitters; isolating the beams of light in the image using color filtering and threshold algorithms; and locating the positions of the beams of light.

16. The method of claim 15 wherein the beams of light present curves on the rail and wherein the step of continuously measuring the minimum distance further comprises the steps of: fitting each curve of each optical emitter with a second order polynomial; and determining the minimum distance between the polynomials analytically.

* * * * *

UNITED STATES PATENT AND TRADEMARK OFFICE
CERTIFICATE OF CORRECTION

PATENT NO. : 7,755,774 B2  Page 1 of 1
APPLICATION NO. : 12/138046
DATED : July 13, 2010
INVENTOR(S) : Shane Farritor et al.

It is certified that error appears in the above-identified patent and that said Letters Patent is hereby corrected as shown below:

Column 1 at line 5, add "This invention was made with government support under grant DTFR53-02G-0015 awarded by the Federal Railroad Administration. The government has certain rights in the invention."

Signed and Sealed this

Twenty-fourth Day of August, 2010

David J. Kappos
*Director of the United States Patent and Trademark Office*